United States Patent [19]

Chu

[11] Patent Number: 4,616,019
[45] Date of Patent: Oct. 7, 1986

[54] NAPHTHYRIDINE ANTIBACTERIAL COMPOUNDS

[75] Inventor: Daniel T. Chu, Vernon Hills, Ill.

[73] Assignee: Abbott Laboratories, North Chicago, Ill.

[21] Appl. No.: 784,286

[22] Filed: Oct. 4, 1985

Related U.S. Application Data

[63] Continuation of Ser. No. 574,120, Jan. 26, 1984, abandoned.

[51] Int. Cl.[4] ............ A61K 31/44; C07D 471/04
[52] U.S. Cl. .................... 514/254; 514/211;
514/218; 514/222; 514/226; 514/232; 514/234;
514/236; 514/257; 514/300; 544/54; 544/58.6;
544/127; 544/238; 544/333; 544/362; 544/405;
546/123
[58] Field of Search ............... 546/123; 544/54, 58.6,
544/238, 127, 333, 362, 405; 260/244.4;
514/211, 218, 222, 226, 232, 234, 236, 254, 257,
300

[56] References Cited

U.S. PATENT DOCUMENTS 4,448,962 5/1984 Irikura et al. .................... 544/362

Primary Examiner—Henry R. Jiles
Assistant Examiner—Bernard I. Dentz
Attorney, Agent, or Firm—Steven F. Weinstock; Martin L. Katz

[57] ABSTRACT

Naphthyridine compounds having the formula:

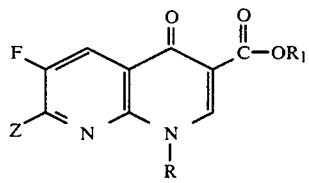

wherein Z is an amine or an aliphatic heterocyclic group, R is a phenyl group or an aromatic heterocyclic group and $R_1$ is hydrogen or a carboxy protecting group. The compounds of the invention have antibacterial activity.

22 Claims, No Drawings

NAPHTHYRIDINE ANTIBACTERIAL COMPOUNDS

This is a continuation of U.S. patent application, Ser. No. 574,120, filed Jan. 26, 1984 now abandoned.

This invention relates to new naphthyridine derivatives having antibacterial properties, compositions containing the new naphthyridine derivatives and methods of treating mammalian patients with the new naphthyridine derivatives.

It is known that certain naphthyridine compounds exhibit antibacterial properties, notably certain 7-piperazinyl-4-oxo-1,8-naphthyridine-3-carboxylic acids. In European Pat. No. 9,425, there are disclosed certain 7-piperazinyl-6-fluoro-1,4-dihydro-4-oxo-1,8-naphthyridine-3-carboxylic acid derivatives which are substituted in the 1 position with an alkyl or vinyl substituent.

This invention relates to novel antibacterial agents and, more particularly, to 7-substituted amino-6-fluoro-1,4-dihydro-4-oxo-1,8-naphthyridine-3-carboxylic acids and derivatives thereof having the formula:

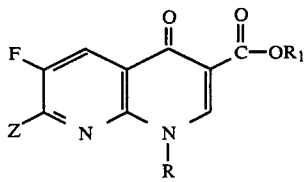

(I)

wherein R is selected from the group consisting of an aromatic heterocyclic ring having 5 to 6 atoms of which 1 or 2 atoms are independently selected from S, O and N and the remaining atoms being carbon atoms; substituted derivatives of the aromatic heterocyclic ring wherein the aromatic heterocyclic ring is monosubstituted with $C_1$ to $C_6$ alkyl; and a phenyl group of the formula:

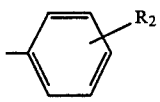

(II)

wherein $R_2$ is one, two or three substituents independently selected from hydrogen, halogen, $C_1$ to $C_6$ alkyl, halo-substituted $C_1$ to $C_6$ alkyl, cyano, methylenedioxy, a group having the formula —Y—$R_3$ wherein —Y— is —O— or —S— and $R_3$ is hydrogen or $C_1$ to $C_6$ alkyl, and an amine having the formula:

wherein
$R_4$ and $R_5$ are each independently hydrogen or $C_1$ to $C_6$ alkyl.

$R_1$ is hydrogen or a carboxy-protecting group.

Z is an amino group having the formula:

wherein
$R_6$ is hydrogen or $C_1$ to $C_6$ alkyl, and $R_7$ is $C_1$ to $C_6$ alkyl, $NH_2$, mono-($C_1$-$C_4$)alkylamino or di-($C_1$-$C_4$)alkylamino.

Alternatively, Z can be an aliphatic heterocyclic ring having 5 to 7 atoms and, in particular, 1 or 2 hetero atoms which are independently selected from the group consisting of S, O, N and combinations thereof, with the remaining atoms in the aliphatic heterocyclic ring being carbon atoms. More particularly, the aliphatic heterocyclic ring has the formula:

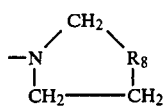

wherein $R_8$ is selected from the group consisting of $CH_2$, $(CH_2)_2$ and a group of the formula —$(CH_2)_nR_9$— wherein $R_9$ is selected from the group consisting of —S—, —O— and —N— and n is 0, 1, or 2. Also included are substituted derivatives of such aliphatic heterocyclic rings wherein the aliphatic heterocyclic ring is substituted with one, two or three substituents independently selected from $C_1$ to $C_6$ alkyl, an amine group having the formula:

wherein $R_{10}$ and $R_{11}$ are each independently selected from the group consisting of hydrogen, $C_1$ to $C_6$ alkyl; hydroxy-substituted $C_1$ to $C_6$ alkyl, $C_1$ to $C_3$ alkylamino-substituted $C_1$ to $C_6$ alkyl, hydroxy, halogen, alkanoyl, alkanoylamido and amino-substituted $C_1$ to $C_6$ alkyl.

Representative aromatic heterocyclic groups include pyridyl, pyrazinyl, thiazoyl, furyl and thienyl.

Illustrative of such aliphatic heterocyclic groups are piperazinyl groups, piperidinyl groups, pyrrolidinyl groups, morpholino groups, thiomorpholino groups and homopiperazinyl groups (i.e., hexahydro-1-H-1,4-diazepinyl).

Representative —Y—$R_3$ groups include hydroxy, mercapto, loweralkoxy, such as methoxy, ethoxy, propoxy, etc., as well as thio analogs thereof, namely methylmercapto, ethylmercapto, etc.

As used herein, the term "halogen" refers to chloro, bromo, fluoro and iodo groups, while the term "$C_1$ to $C_6$ alkyl" refers to lower alkyl groups including methyl, ethyl, propyl, isopropyl, butyl, etc.

As used herein "$C_1$ to $C_6$ alkyl" includes both branched or straight chained alkyl. Representative of halo-substituted and hydroxy-substituted $C_1$ to $C_6$ alkyls include chloromethyl, chloroethyl, chloropropyl, hydroxyethyl, trifluoromethyl, etc.

As used herein, the term "alkanoyl" refers to

wherein $R_{12}$ is $C_1$ to $C_6$ alkyl.

As used herein, the term "alkanoylamido" refers to

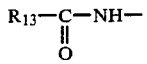

wherein $R_{13}$ is $C_1$ to $C_6$ alkyl.

As used herein, the term "carboxy-protecting group" refers to a carboxy group which has been esterified with one of the commonly used carboxylic acid protecting ester groups employed to block or protect the carboxylic acid functionality while reactions involving other functional sites of the compound are carried out. In addition, a carboxy protecting group can be used as a prodrug whereby the carboxy protecting group can be hydrolyzed enzymatically to release the biologically active parent acid. Such protected carboxy groups are noted for their ease of cleavage by hydrolytic methods to the corresponding carboxylic acid. Further, such carboxy-protecting groups can be relatively easily cleaved to yield the corresponding free carboxy group. Such carboxy-protecting groups are well known to those skilled in the art, having been extensively used in the protection of carboxyl groups in the penicillin and cephalosporin fields, as described in U.S. Pat. Nos. 3,840,556 and 3,719,667, the disclosures of which are incorporated herein by reference. Representative protecting groups include $C_1$ to $C_8$ alkyl (e.g., methyl, ethyl, tertiary butyl), benzyl and substituted derivatives thereof such as alkoxy and nitrobenzyl groups, dialkylaminoalkyl (e.g. dimethylaminoethyl), acyloxyalkyl groups such as pivaloyloxymethyl and propionyloxy methyl.

The chiral centers of the compounds of the invention may have either the "R" "S" configuration.

Representative of the preferred compounds of the invention include 1-phenyl-6-fluoro-1,4-dihydro-4-oxo-7(1-piperazinyl)-1,8-naphthyridine-3-carboxylic acid, 1-phenyl-6-fluoro-1,4-dihydro-4-oxo-7-(1-4methyl)-piperazinyl-1,8-naphthyridine-3-carboxylic acid, 1-p-fluorophenyl-6-fluoro-1,4-dihydro-4-oxo-7(1-piperazinyl)-1,8-naphthyridine-3-carboxylic acid, 1-(3,4-dichloro)phenyl-6-fluoro-1,4-dihydro-4-oxo-7(1-piperazinyl)-1,8-naphthyridine-3-carboxylic acid, 1-p-hydroxyphenyl-6-fluoro-1,4-dihydro-4-oxo-7(1-piperazinyl)-1,8-naphthyridine-3-carboxylic acid, 1-p-fluorophenyl-6-fluoro-1,4-dihydro-4-oxo-7-(1-4-methyl)piperazinyl-1,8-naphthyridine-3-carboxylic acid, 1-o,p-difluorophenyl-6-fluoro-1,4-dihydro-4-oxo-7-(3-methyl-1-piperazinyl)-1,8-naphthyridine-3-carboxylic acid, 1-o,p-difluorophenyl-6-fluoro-1,4-dihydro-4-oxo-7(3-amino-1-pyrrolidinyl)-1,8-naphthyridine-3-carboxylic acid, 1-o,p-difluorophenyl-6-fluoro-1,4-dihydro-4-oxo-7(3-amino-4-methyl-1-pyrrolidinyl)-1,8-naphthyridine-3-carboxylic acid and 1-o,p-difluorophenyl-6-fluoro-1,4-dihydro-4-oxo-7(cis-3-aminomethyl-4-chloro-1-pyrrolidinyl)-1,8-naphthyridine-3-carboxylic acid.

Also included within the scope of the present invention are pharmaceutically acceptable salts of the foregoing compounds. As used herein, the term "pharmaceutically acceptable salts" refers to non-toxic acid addition salts and alkaline earth metal salts of the compounds of formula I. The salts can be prepared in situ during the final isolation and purification of the compounds of formula I, or separately by reacting the free base or acid functions with a suitable organic acid or base. Representative acid addition salts include the hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate, glucoheptonate, lactobionate, lauryl sulfate salts and the like. Representative alkali or alkaline earth metal salts include the sodium, calcium, potassium and magnesium salts, etc. It has been found that the compounds of the present invention possess antibacterial activity against a wide spectrum of gram positive and gram negative bacteria, as well as enterobacteria. The compounds of the invention are therefor useful in the antibiotic treatment of susceptible bacterial infections in both humans and animals. In addition, the compounds, by reason of their in vitro activity, may be used in scrub solutions for surface inhibition of bacterial growth.

Susceptible organisms generally include those gram positive and gram negative, aerobic and anaerobic organisms whose growth can be inhibited by the compounds of the invention such as Staphylococcus, Lactobacillus, Streptococcus, Sarcina, Escherichia, Enterobacter, Klebsiella, Pseudomonas, Acinetobacter, Proteus, 15 Citrobacter, Nisseria, Baccillus, Bacteroides, Peptococcus, Clostridium, Salmonella, Shigella, Serratia, Haemophilus, Brucella, and other organisms. In addition to exhibiting highly effective antibacterial activity, the compounds of the invention exhibit increased and improved solubility characteristics as compared with prior naphthyridine-3-carboxylic acid compounds in the art.

The compounds of Formula I may also be formulated into compositions together with pharmaceutically acceptable carriers for parenteral injection, for oral administration in solid or liquid form, for rectal administration, and the like.

Compositions according to the invention for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters such as ethyl oleate. Such compositions may also contain adjuvants such as preserving, wetting, emulsifying, and dispersing agents. They may be sterilized, for example, by filtration through a bacteria-retaining filter, or by incorporating sterilizing agents into the compositions. They can also be manufactured in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixers containing inert diluents commonly used in the art, such as water. Besides such inert diluents, compositions can also include adjuvants, such as wetting agents, emulsifying and suspending agents, and sweetening, flavoring and perfuming agents.

Compositions for rectal administration are preferably suppositories which may contain, in addition to the active substance, excipients such as cocoa butter or a suppository wax.

Actual dosage levels of active ingredient in the compositions of the invention may be varied so as to obtain an amount of active ingredient effective to achieve antibacterial activity in accordance with the desired method of administration. The selected dosage level therefore depends upon the nature of the active compound administered, the route of administration, the desired duration of treatment and other factors. Generally, daily dosage levels of the compounds of Formula I of about 0.1 to about 750, more preferably about 0.25 to about 500 and most preferably about 0.5 to about 300 mg. of active ingredient per kg. of body weight are effective when administered orally to a mammalian patient suffering from an infection caused by a susceptible organism. If desired, the daily dose may be divided into multiple doses for administration, e.g., two to four times per day.

Compounds according to this invention can be prepared by the reaction illustrated below:

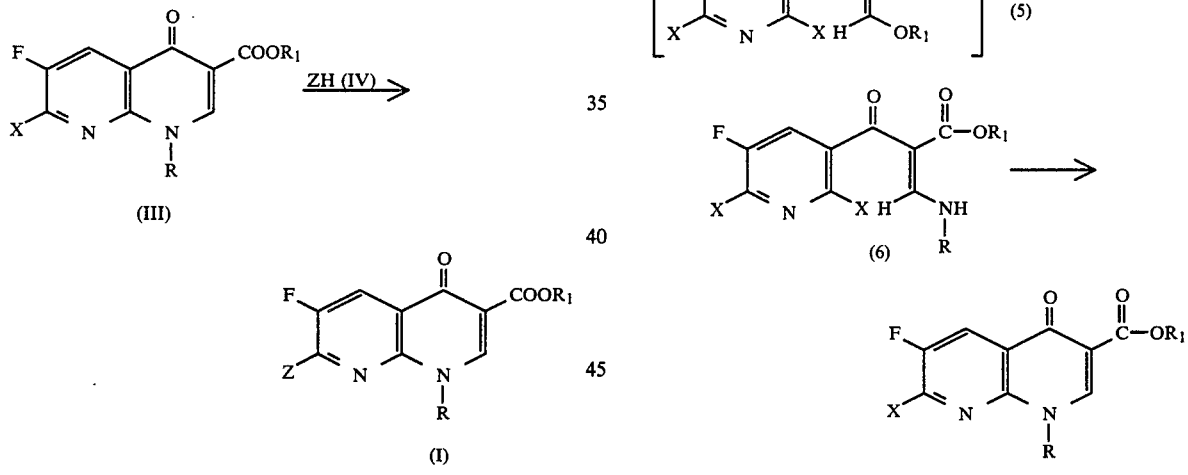

wherein X is a halogen or mesylate or methoxy group and R, $R_1$ and Z are the same as described above.

The reaction may be performed by heating a compound of the formula (III) with an amine of formula (IV) at a temperature of from 20° C. to 150° C., in the presence of a suitable organic polar or non-polar solvent such as dimethylsulfoxide, sulfolane, dimethylformamide, pyridine, dimethylacetamide, 1-methyl-2-pyrrolidinone, waer, tetrahydrofuran or methylene chloride. It is desirable to carry out the reaction in the presence of an acid-acceptor such as triethylamine, potassium carbonate and the like at a molar ration of 1.0 to 1.2 moles of the acid-acceptor per mole of the compound of the formula (III). The amine (IV) can also be used as acid acceptor in which 2 or more molar excess of this reagent is used. The compounds of the formula (III) may be prepared in accordance with the following reaction scheme, in which X, R are as described above.

In accordance with the foregoing reaction scheme, the the known nicotinic acid ester (1) is hydrolyzed with mineral acid to the free acid (2) which can then be converted to its acid chloride (2A) by treatment with thionyl chloride. Displacement of the acid chloride (2A) with malonic acid half ester (D) in the presence of n-butyl lithium yields the beta-ketoester (3).

The beta-ketoester (3) is then treated with a trialkylorthoformate (4) in the presence of an acid anhydride, preferably acetic anhydride, followed by reaction with substituted or unsubstituted amine (5) to obtain the enaminoketoester (6). In the trialkylorthoformate (4), R1 may be an alkyl group of, for example, from 1 to 10 carbon atoms, but is preferably loweralkyl, such as ethyl. Reaction with the trialkylorthoformate is preferably conducted at elevated temperatures, such as from about 50° C. to about 150° C., preferably from about 100° C. to about 140° C., to obtain an oily liquid, which may be isolated or unisolated, as desired (shown in brackets in the reaction scheme). Reaction of the latter with the substituted or unsubstituted amine (5) is preferably conducted in an appropriate aprotic or non-aprotic solvent, preferably methylene chloride or tetrahydrofuran, and may be conducted at room or suitable elevated temperature, as desired.

The enaminoketoester (6) is then cyclized, such as by treatment with a strong base as defined above, preferably sodium hydride, to obtain the 1,4-dihydro-4-oxo-1,8-naphthyridine-3-carboxylic acid ester (III). Cyclization is conducted in the the presence of an aprotic solvent, such as dimethoxyethane, bis(2-methoxyethyl)ether, dimethylformamide, tetrahydrofuran or chlorobenzene, and is preferably conducted at temperatures of about 20° C. to about 145° C., more preferably at the reflux temperature of the solvent employed.

The ester (III) ($R_1$=alkyl) can also be subjected to hydrolysis, such as by treatment with sodium hydroxide, or dilute mineral acid to form the free acid (III) ($R_1$=H).

The 1,4-dihydro-4-oxo-1,8-naphthyridine-3-carboxylic acid (I, $R_1$=H) can then be converted into the corresponding ester, if desired, by conventional esterification procedures, such as by treating the free acid (I, $R_1$=H) with the appropriate alcohol in the presence of an acid catalyst, by converting the free acid (I, $R_1$=H) into the corresponding acid chloride followed by displacement of the chloro radical with the appropriate alcohol, or by treating the sodium salt of the acid (I, $R_1$=H) with a suitable reactive halide, such as chloro-methylpivalate in dimethoxyethane to obtain, for example, the pivaloyloxymethyl ester (I) where $R_1$ is —$CH_2OCOC(CH_3)_3$.

The foregoing may be better understood from the following examples, which are presented for purposes of illustration and are not intended to limit the scope of the inventive concepts. As used in the following examples, the references to compounds, such as (1), (2), (3), etc., and to substituents, such as R, $R_1$, $R_2$, etc., refer to the corresponding compounds and substituents in the foregoing reaction scheme and in formulae I, II and III.

EXAMPLE 1

1-Phenyl-6-fluoro-1,4-dihydro-4-oxo-7-(1-piperazinyl)-1,8-naphthyridine-3-carboxylic acid (a) To a solution of 1.0 g of dichlorofluoro nicotinic acid ester (1) (X=Cl, $R_1$=$C_2H_5$) in 5 ml. of trifluoroacetic acid, 6 ml. 6N HCl is added. The solution is heated for 16 hours and cooled and extracted with a methylene chloride. The methylene chloride solution is extracted with saturated sodium bicarbonate solution. The aqueous extract is acidified to pH 3 and then extracted with methylene chloride. After drying, it yields 0.767 g. pale yellow solid (2) (X=Cl). This compound (2) (0.5 g.) is then suspended in 10 ml. benzene and 1.7 ml. of thionyl chloride and 2 drops of dimethylformamide. After refluxing for 30 minutes, the reaction mixture is evaporated to dryness to give the acid chloride (2A). This is added to a solution of 2.54 g. of ethyl malonate monoester in 20 ml. of THF solution containing 0.52 g. of n-butyl lithium at −65° C. The solution is allowed to warm up to room temperature, and then acidified and extracted with ether. The ether extract is washed with saturated $NaHCO_3$ and then water, and dried to yield 0.49 g. of the ketoester (3) (X=Cl, $R_1$=$C_2H_5$).

(b) A solution of 3.8 g. of beta-ketoester (3) ($R_1$=$C_2H_5$ X=Cl) in 3.5 ml. of triethylorthoformate and 10 ml. of acetic anhydride is heated at 135° C. for 1½ hours with the removal of the ethyl acetate formed during the reaction. The solution is evaporated under reduced pressure to a mobile oil. The oil is then dissolved in 150 ml. of methylene chloride and 1.5 ml. of aniline is added into the solution. After 1 hour, the solution is evaporated to dryness and purified through silica gel column yielding 3.7 g. (6), wherein $R_1$=$C_2H_5$ and R=phenyl, X=Cl).

(c) To a cold solution of 3.5 g. of the preceding product (6), $R_1$=C R=phenyl, X=Cl, in 100 ml. tetrahydrofuran is slowly added 240 mg. of a 60% sodium hydride-in-oil suspension. It is then heated for 1 hour and cooled, and 1 liter of water is added. The mixture is then filtered and the solid is washed with a 1:1 hexane/ether solution to obtain 2.1 g. (III) wherein $R_1$=$C_2H_5$, R=phenyl, X=Cl.

(d) To a suspension of 5.2 g. of (III) ($R_1$=$C_2H_5$, R=phenyl, X=Cl) in 30 ml. THF is added a sodium hydroxide solution (0.74 g. in 20 ml. $H_2O$). The mixture is heated at 80° C. for 1 hour resulting in a clear solution which is evaporated under reduced pressure to dryness. The solid is dissolved in 200 ml. $H_2O$, and 2 ml. acetic acid is added. The resulting precipitate is filtered and washed with cold water, crystallized to produce 7-chloro-1-phenyl-6-fluoro-1,4-dihydro-4-oxo-1,8-naphthyridine-3-carboxylic acid (III) (R=phenyl, X=Cl, $R_1$=H).

(e) To a solution of 2.0 g. of 7-chloro-1-phenyl-6-fluoro-1,4-dihydro-4-oxo-1,8-naphthyridine-3-carboxylic acid in 20 ml. of 1-methyl-2-pyrrolidinone at 65° C. is added 2 ml. piperazine. After stirring at 65° C. for 20 hours, the solvent is removed by reduced pressure to dryness. Ethanol is added to the residue and the resulting mixture is filtered and washed with ether and then washed with very small amounts of cold water to give (I)

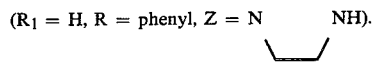

($R_1$ = H, R = phenyl, Z = N⟩NH).

The resulting dried solid is suspended in 30 ml. $H_2O$ and 5 ml. 1N HCl is added to and warmed to dissolve. Removal of the solvent under reduced pressure gives hydrochloride salt of 1-phenyl-6-fluoro-1,4-dihydro-4-oxo-7-(1-piperazinyl)-1,8-naphthyridine-3-carboxylic acid (1)

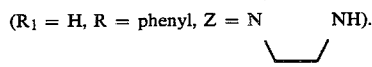

($R_1$ = H, R = phenyl, Z = N⟩NH).

To the hydrochloride salt is added one molar equivalent of an aqueous solution of sodium hydroxide, and the resulting precipitate is filtered to obtain 1-phenyl-6-fluoro-1,4-dihydro-4-oxo-7-(1-piperazinyl)-1,8-naphthyridine-3carboxylic acid.

(f) Alternately, the title compound is prepared as follows: To a solution of 1.6 g. of compound (III) ($R_1$=$C_2H_5$, R=phenyl, X=Cl) (product of 1(c) in 50 ml. of methylene chloride is added 1 ml. of triethylamine and 710 mg. of N-acetylpiperazine. After heating for 2 hours, the solvent is washed with 50 ml. of 1N HCl solution and then with water. The methylene chloride solution is dried and evaporated to dryness, yielding 2.1 g. of compound (I)

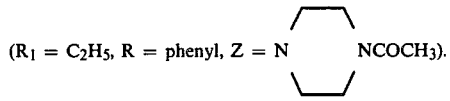

A suspension of 2.1 g. of the preceding compound (I) in 25 ml. of 3N HCl solution is heated at 80° C. for 6 hours. The solvent is removed giving the hydrochloride salt of (I) ($R_1$=H, R=phenyl, Z=N NH). The solid is dissolved in 100 ml. water. The pH of the solution is adjusted to pH 7 by the addition of 10% sodium hydroxide. The precipitate is filtered and washed with cold water yielding 1.8 g. of 1-phenyl-6-fluoro-1,4-dihydro-4-oxo-7-(1-piperazinyl)-1,8-naphthyridine-3-carboxylic acid

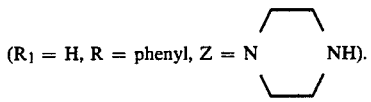

EXAMPLE 2

1-phenyl-6-fluoro-1,4-dihydro-4-oxo-7-(4-acetyl-1-piperazinyl)-1,8-naphthyridine-3-carboxylic acid In the described fashion as Example 1(f), one can obtain the intermediate (I)

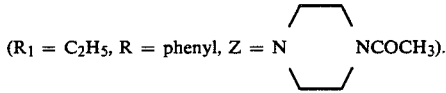

A solution of 2.1 g of this compound in 30 ml THF and 200 mg of sodium hydride in 5 ml $H_2O$ is heated at reflux for 8 hours. The solvent is evaporated off at reduced pressure and the residue is redissolved in 200 ml water. Acidification with acetic acid yields a precipitate which is filtered to give 1-phenyl-6-fluoro-1,4-dihydro-4-oxo-7-(4-acetyl-1-piperazinyl)-1,8-naphthyridine-3-carboxylic acid

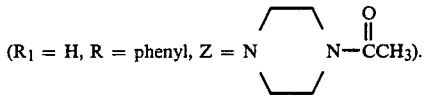

EXAMPLE 3

1-phenyl-6-fluoro-1,4-dihydro-4-oxo-7-(1-(4-methyl)-piperazinyl)-1,8-naphthyridine-3-carboxylic acid The procedure of Example 1 can be repeated, replacing N-acetylpiperazine in Example 1(f) with N-methyl-piperazine to obtain 1-phenyl-6-fluoro-1,4-dihydro-4-oxo-7-(1-(4-methyl)piperazinyl)-1,8-naphthyridine-3-carboxylic acid (1)

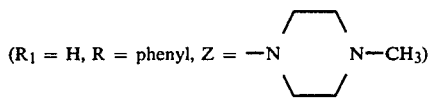

and its hydrochloride salt.

EXAMPLE 4

1-phenyl-6-fluoro-1,4-dihydro-4-oxo-7(1-pyrrolidinyl)-1,8-naphthyridine-3-carboxylic acid In the described fashion as Example 1 replacing piperazine in Example 1(e) with pyrrolidine, one can obtain 1-phenyl-6-fluoro-1,4-dihydro-4-oxo-7(1-pyrrolidinyl)-1,8naphthyridine-3-carboxylic acid in good yield (I)

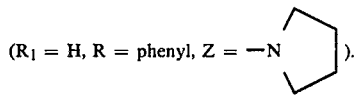

EXAMPLE 5

1-phenyl-6-fluoro-1,4-dihydro-4-oxo-7-(3-hydroxy-1-pyrrolidinyl)-1,8-naphthyridine-3-carboxylic acid The procedure of Example 1 can be repeated replacing piperazine in Example 1(e) with 3-hydroxypyrrolidine to obtain 1-phenyl-6-fluoro-1,4-dihydro-4-oxo-7-(3-hydroxy-1-pyrrolidinyl)-1,8-naphthyridine-3-carboxylic acid (I)

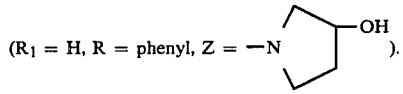

EXAMPLE 6

1-phenyl-6-fluoro-1,4-dihydro-4-oxo-7-(3-amino-1-pyrrolidinyl)-1,8-naphthyridine-3-carboxylic acid In the described fashion as Example 1 replacing N-acetylpiperazine in Example 1(f) with 3-acetamido-pyrrolidine, one can obtain 1-phenyl-6-fluoro-1,4-dihydro-4-oxo-7-(3-amino-1-pyrrolidinyl)-1,8-naphthyridine-3-carboxylic acid hydrochloride salt (I)

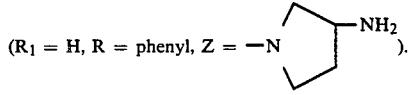

EXAMPLE 7

1-phenyl-6-fluoro-1,4-dihydro-4-oxo-7-(1-piperidinyl)-1,8-naphthyridine-3-carboxylic acid The procedure of Example 1 can be repeated replacing piperazine in Example 1(e) with piperidine to obtain 1-phenyl-6-fluoro-1,4-dihydro-4-oxo-7-(1-piperidinyl)-1,8-naphthyridine-3-carboxylic acid (I)

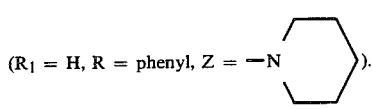($R_1$ = H, R = phenyl, Z = —N⟨ ⟩).

EXAMPLE 8

1-phenyl-6-fluoro-1,4-dihydro-4-oxo-7-(3-acetamido-1-pyrrolidinyl)-1,8-naphthyridine-3-carboxylic acid In the described fashion as Example 1, replacing N-acetylpiperazine in Example 1(f) with 3-acetomido-pyrrolidine, one can obtain the ester (I)

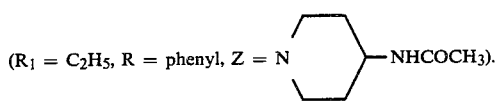($R_1$ = $C_2H_5$, R = phenyl, Z = N⟨ ⟩—NHCOCH$_3$).

Following the procedure of Example 2 this ester (I) yields 1-phenyl-6-fluoro-1,4-dihydro-4-oxo-7-(3-acetamido-1-pyrrolidinyl)-1,8-naphthyridine-3-carboxylic acid.

EXAMPLE 9

1-phenyl-6-fluoro-1,4-dihydro-4-oxo-7-(4-morpholinyl)-1,8-naphthyridine-3-carboxylic acid In the described fashion as Example 1 replacing piperazine in Example 1(e) with morpholine, one can obtain 1-phenyl-6-fluoro-1,4-dihydro-4-oxo-7-(4-morpholinyl)-1,8-naphthyridine-3-carboxylic acid (I)

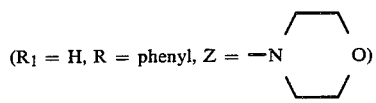($R_1$ = H, R = phenyl, Z = —N⟨ ⟩O)

in good yield.

EXAMPLE 10

1-phenyl-6-fluoro-1,4-dihydro-4-oxo-7-(4-thiomorpholinyl)-1,8-naphthyridine-3-carboxylic acid The procedure of Example 1 can be repeated replacing piperazine in Example 1(e) with thiomorpholine to obtain 1-phenyl-6-fluoro-1,4-dihydro-4-oxo-7-(4-thiomorpholinyl)-1,8-naphthyridine-3-carboxylic acid (I)

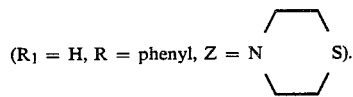($R_1$ = H, R = phenyl, Z = N⟨ ⟩S).

EXAMPLE 11

1-phenyl-6-fluoro-1,4-dihydro-4-oxo-7-(3,5-dimethyl-1-piperazinyl)-1,8-naphthyridine-3-carboxylic acid In the described fashion as Example 1 replacing N-acetylpiperazinyl in Example 1(f) with 2,6-dimethyl piperazine, one can obtain 1-phenyl-6-fluoro-1,4-dihydro-4-oxo-7-(3,5-dimethyl-1-piperazinyl)-1,8-naphthyridine-3-carboxylic acid a hydrochloride salt (I)

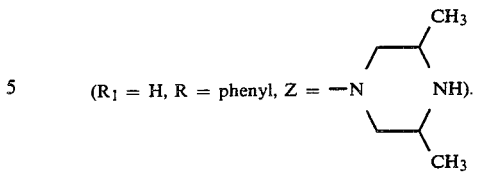($R_1$ = H, R = phenyl, Z = —N⟨ ⟩NH).

EXAMPLE 12

1-phenyl-6-fluoro-1,4-dihydro-4-oxo-7-(1-homopiperazinyl)-1,8-naphthyridine-3-carboxylic acid The procedure of Example 1 can be repeated replacing N-acetylpiperazine in Example 1(f) with homopiperazine to obtain 1-phenyl-6-fluoro-1,4-dihydro-4-oxo-7-(1-homopiperazinyl)-1,8-naphthyridine-3-carboxylic acid and its hydrochloride salt (I)

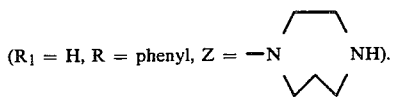($R_1$ = H, R = phenyl, Z = —N⟨ ⟩NH).

EXAMPLE 13

1-phenyl-6-fluoro-1,4-dihydro-4-oxo-7-(dimethylamino)-1,8-naphthyridine-3-carboxylic acid In the described fashion as Example 1 replacing piperazine in Example 1(e) with dimethylamine, one can obtain 1-phenyl-6-fluoro-1,4-dihydro-4-oxo-7-(dimethylamino)-1,8-naphthyridine-3-carboxylic acid (I) ($R_1$=H, R=phenyl, Z=—N(CH$_3$)$_2$).

EXAMPLE 14

1-phenyl-6-fluoro-1,4-dihydro-4-oxo-7-(N-2-hydroxyethylamino)-1,8-naphthyridine-3-carboxylic acid The procedure of Example 1 can be repeated replacing piperazine in Example 1(e) with N-2-hydroxyethylamine to obtain 1-phenyl-6-fluoro-1,4-dihydro-4-oxo-7-(N-2-hydroxyethylamino)-1,8-naphthyridine-3-carboxylic acid (I) ($R_1$=H, R=phenyl, Z=—NHC$_2$H$_4$—OH).

EXAMPLE 15

1-phenyl-6-fluoro-1,4-dihydro-4-oxo-7-(hydrazyl)-1,8-naphthyridine-3-carboxylic acid In the described fashion as Example 1 replacing piperazine in Example 1(e) with hydrazine, one can obtain 1-phenyl-6-fluoro-1,4-dihydro-4-oxo-7-(hydrazyl)-1,8-naphthyridine-3-carboxylic acid and its hydrochloride salt (I) $R_1$=H, R=phenyl, Z=—NHNH$_2$).

EXAMPLE 16

1-phenyl-6-fluoro-1,4-dihydro-4-oxo-7-(2,2-dimethylhydrazyl)-1,8-naphthyridine-3-carboxylic acid The procedure of Example 1 can be repeated replacing piperazine in Example 1(e) with 1,1-dimethylhydrazine to obtain 1-phenyl-6-fluoro-1,4-dihydro-4-oxo-7-(2,2-dimethylhydrazyl)-1,8-naphthyridine-3-carboxylic acid and its hydrochloride salt (I) ($R_1$=H, R=phenyl, Z=NH—N(CH$_3$)$_2$).

EXAMPLE 17

1-p-Fluorophenyl-6,fluoro-1,4-dihydro-4-oxo-7-(1-piperazinyl)-1,8-naphthyridine-3-carboxylic acid (a) In the described fashion as Example 1(b) replacing aniline with p-fluroaniline, one can obtain the enaminoketoester (6) ($R_1=C_2H_5$, R=p-fluorophenyl, X=Cl).

(b) By following the Example 1(c), the preceding compound(s) can yield 7-chloro-1-p-fluorophenyl-6-fluoro-1,4-dihydro-4-oxo-1,8-naphthyridine-3-carboxylic acid ester (III) (R=p-fluorophenyl, X=Cl, $R_1=C_2H_5$).

(c) In the described fashion as Example 1(f) the above ester (III) reacting with N-acetylpiperazine can give the desired 1-p-fluorophenyl-6-fluoro-1,4-dihydro-4-oxo-7-(1-piperazinyl)-1,8-naphthyridine-3-carboxylic acid (I)

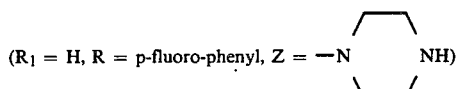

($R_1$ = H, R = p-fluoro-phenyl, Z = —N⌐⌐NH)

and its hydrochloride salt.

EXAMPLE 18

In the described fashion as Example 1(f), replacing the ester (III) (R=phenyl, X=Cl, $R_1=C_2H_5$) with the ester (III) of the product of Example 17(b) (R=p-fluorophenyl, X=Cl, $R_1=C_2H_5$) and also replacing N-acetylpiperazine with an appropriate amine such as N-methylpiperazine, 3-acetamido-4-methylpyrrolidine, 3-hydroxy-pyrrolidine, 3-acetamidopyrrolidine, piperidine, morpholine, thiomorpholine, 2-methyl piperazine, homopiperazine, diethylamine, 2,2-dimethylhydrazine and cis-3-aminomethyl-4-chloro-1-pyrrolidine, one can obtain the following compounds:

(a) 1-p-fluorophenyl-6,fluoro-1,4-dihydro-4-oxo-7-(4-methyl-1-piperazinyl)-1,8-naphthyridine-3-carboxylic acid (I)

($R_1$ = H, R = p-fluorophenyl, Z = —N⌐⌐N—$CH_3$).

(b) 1-p-fluorophenyl-6-fluoro-1,4-dihydro-4-oxo-7-(3-amino-4-methyl-1-pyrrolidinyl)-1,8-naphthyridine-3-carboxylic acid (I)

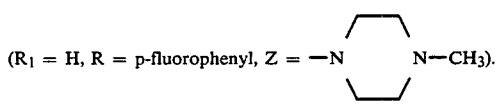

(c) 1-p-fluorophenyl-6-fluoro-1,4-dihydro-4-oxo-7-(3-hydroxy-1-pyrrolidinyl)-1,8-naphthyridine-3-carboxylic acid (I)

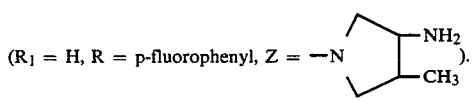

(d) 1-p-fluorophenyl-6-fluoro-1,4-dihydro-4-oxo-7-(3-amino-1-pyrrolidinyl)-1,8-naphthyridine-3-carboxylic acid (I)

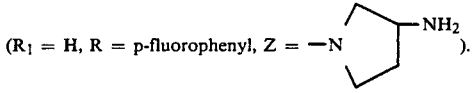

(e) 1-p-fluorophenyl-6-fluoro-1,4-dihydro-4-oxo-7-(1-piperidinyl)-1,8-naphthyridine-3-carboxylic acid (I)

($R_1$ = H, R = p = fluorophenyl, Z = —N⌐⌐).

(f) 1-p-fluorophenyl-6-fluoro-1,4-dihydro-4-oxo-7-(4-morpholinyl)-1,8-naphthyridine-3-carboxylic acid (I)

($R_1$ = H, R = p-fluorophenyl, Z = —N⌐⌐O).

(g) 1-p-fluorophenyl-6-fluoro-1,4-dihydro-4-oxo-7-(4-thiomorpholinyl)-1,8-naphthyridine-3-carboxylic acid (I)

($R_1$ = H, R = p-fluorophenyl, Z = —N⌐⌐S).

(h) 1-p-fluorophenyl-6-fluoro-1,4-dihydro-4-oxo-7-(3-methyl-1-piperazinyl)-1,8-naphthyridine-3-carboxylic acid (I)

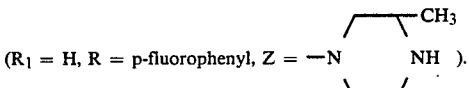

(i) 1-p-fluorophenyl-6-fluoro-1,4-dihydro-oxo-7-(1-homopiperazinyl)-1,8-naphthyridine-3-carboxylic acid (I)

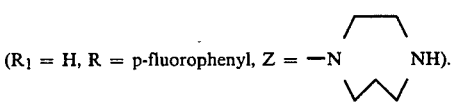

(j) 1-p-fluorophenyl-6-fluoro-1,4-dihydro-4-oxo-7-(diethylamino)-1,8-naphthyridine-3-carboxylic acid (I) ($R_1$=H, R=p-fluorophenyl, Z=—N($C_2H_5$)$_2$).

(k) 1-p-fluorophenyl-6-fluoro-1,4-dihydro-4-oxo-7-(2,2-dimethylhydrazyl)-1,8-naphthyridine-3-carboxylic acid (I). ($R_1$=H, R=p-fluorophenyl, Z=—N-H—N(CH$_3$)$_2$).

(l) 1-p-fluorophenyl-6-fluoro-1,4-dihydro-4-oxo-7-(cis-3-aminomethyl-4-chloro-1-pyrrolidinyl)1,8-naphthyridine-3-carboxylic acid (I),

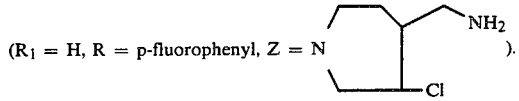

($R_1$ = H, R = p-fluorophenyl, Z = N⟨⟩-CH₂NH₂, -Cl).

EXAMPLE 19

1-o,p-difluorophenyl-6-fluoro-1,4-dihydro-4-oxo-7-(1-piperazinyl)-1,8-naphthyridine-3-carboxylic acid (a) In the described fashion as Example 1(b) replacing aniline with 2,4-difluoroaniline, one can obtain the enaminoketoester (6) ($R_1=C_2H_5$, R=2,4-difluorophenyl, X=Cl).

(b) By following the Example 1(c), the preceding compound (6) can yield 7-chloro-1-o,p-difluorophenyl-6-fluoro-1,4-dihydro-4-oxo-1,8-naphthyridine-3-carboxylic acid ester (III). (R=2,4-difluorophenyl, X=Cl, $R_1=C_2H_5$).

(c) In the described fashion as Example 1(f), the above acid ester (III) reacting with N-acetylpiperazine can give the desired 1-o,p-difluorophenyl-6-fluoro-1,4-dihydro-4-oxo-7-(1-piperazinyl)-1,8-naphthyridine-3-carboxylic acid (I).

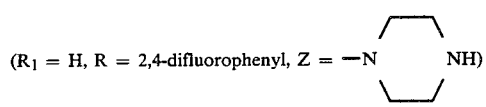

($R_1$ = H, R = 2,4-difluorophenyl, Z = —N⟨⟩NH)

and its hydrochloride salt.

EXAMPLE 20

In the described fashion as Example 1(f), replacing the acid ester (III) (R=phenyl, X=Cl, $R_1=C_2H_5$) with the acid ester (III) of the product of Example 19(b) (R=2,4-difluorophenyl, X=Cl, $R_1=C_2H_5$) and also replacing N-acetylpiperazine with an appropriate amine such as N-methylpiperazine, 3-amino-4-methylpyrrolidine, cis-3-aminomethyl-4-chloropyrrolidine, 3-acetamidopyrrolidine, piperidine, morpholine, thiomorpholine, 2-methylpiperazine, homopiperazine, diethylamine and 3-N-ethyl-N-acetylaminomethyl-1-pyrrolidine, one can obtain the following compounds:

(a) 1-o,p-difluorophenyl-6-fluoro-1,4-dihydro-4-oxo-7-(4-methyl)piperazinyl)-1,8-naphthyridine-3-carboxylic acid (I).

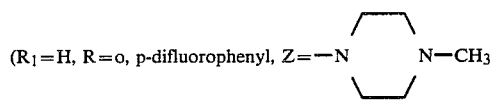

($R_1$=H, R=o, p-difluorophenyl, Z=—N⟨⟩N—CH₃)

and its hydrochloride salt.

(b) 1-o,p-difluorophenyl-6-fluoro-1,4-dihydro-4-oxo-7-(3-amino-4-methyl-1-pyrrolidinyl)-1,8-naphthyridine-3-carboxylic acid (I).

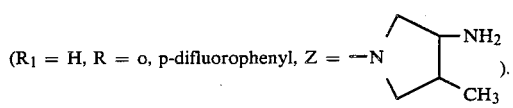

($R_1$ = H, R = o, p-difluorophenyl, Z = —N⟨⟩-NH₂, -CH₃).

(c) 1-o,p-difluorophenyl-6-fluoro-1,4-dihydro-4-oxo-7-(cis-3-aminomethyl-4-chloro-1-pyrrolidinyl)-1,8-naphthyridine-3-carboxylic acid (I).

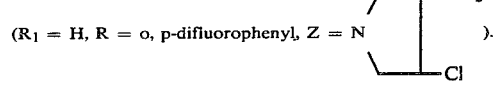

($R_1$ = H, R = o, p-difluorophenyl, Z = N⟨⟩-NH₂, -Cl).

(d) 1-o,p-difluorophenyl-6-fluoro-1,4-dihydro-4-oxo-7-(3-amino-1-pyrrolidinyl)-1,8-naphthyridine-3-carboxylic acid (I).

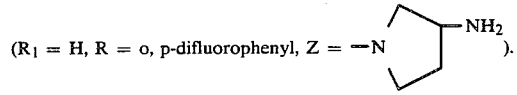

($R_1$ = H, R = o, p-difluorophenyl, Z = —N⟨⟩-NH₂).

(e) 1-o,p-difluorophenyl-6-fluoro-1,4-dihydro-4-oxo-7-(1-piperidinyl)-1,8-naphthyridine-3-carboxylic acid (I).

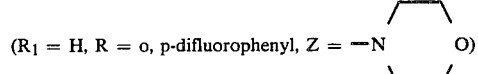

($R_1$ = H, R = o, p-difluorophenyl, Z = —N⟨⟩O)

(f) 1-o,p-difluorophenyl-6-fluoro-1,4-dihydro-4-oxo-7-(4-morpholinyl)-1,8-naphthyridine-3-carboxylic acid (I).

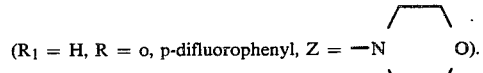

($R_1$ = H, R = o, p-difluorophenyl, Z = —N⟨⟩O).

(g) 1-o,p-difluorophenyl-6-fluoro-1,4-dihydro-4-oxo-7-(4-thiomorpholinyl)-1,8-naphthyridine-3-carboxylic acid (I).

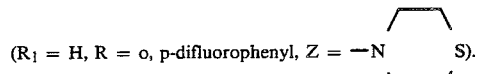

($R_1$ = H, R = o, p-difluorophenyl, Z = —N⟨⟩S).

(h) 1-o,p-difluorophenyl-6-fluoro-1,4-dihydro-4-oxo-7(3-methyl-1-piperazinyl)-1,8-naphthyridine-3-carboxylic acid (I).

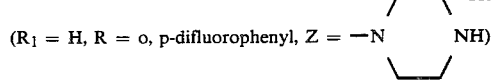

($R_1$ = H, R = o, p-difluorophenyl, Z = —N⟨⟩-CH₃, NH).)

(i) 1-o,p-difluorophenyl-6-fluoro-1,4-dihydro-4-oxo-7-(1-homopiperazinyl)-1,8-naphthyridine-3-carboxylic acid (I).

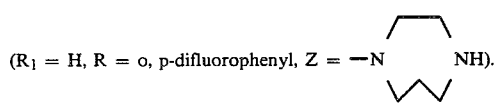

($R_1$ = H, R = o, p-difluorophenyl, Z = —N⟨⟩NH).

(j) 1-o,p-difluorophenyl-6-fluoro-1,4-dihydro-4-oxo-7-(diethylamino)-1,8-naphthyridine-3-carboxylic acid (I). ($R_1$=H, R=o,p-difluorophenyl, Z=—$N(C_2H_5)_2$).

(k) 1-o,p-difluorophenyl-6-fluoro-1,4-dihydro-4-oxo-7-(3-ethylaminomethyl-1-pyrrolidinyl)-1,8-naphthyridine-3-carboxylic acid (I).

($R_1$ = H, R = o, p-difluorophenyl, Z = N 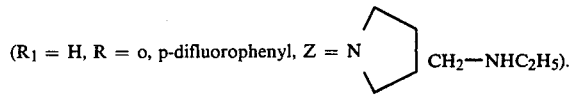 $CH_2$—$NHC_2H_5$).

EXAMPLE 21

In the described fashion as Example 1 (a, b, c), replacing aniline with an appropriate amine (R—$NH_2$), one can obtain the additional 1-substituted, 7-chloro-6-fluoro-1,4-dihydro-4-oxo-1,8-naphthyridine-3-carboxylic acid ester III as listed in Table I.

TABLE I

| | Aniline Replacement (RNH$_2$) | Compound (III) (X = Cl R$_1$ = C$_2$H$_5$) Obtained R |
|---|---|---|
| (a) | o-fluoroaniline | o-fluorophenyl |
| (b) | p-chloroaniline | p-chlorophenyl |
| (c) | o-chloroaniline | o-chlorophenyl |
| (d) | p-methylaniline | p-methylphenyl |
| (e) | p-methoxyaniline | p-methoxyphenyl |
| (f) | 4-hydroxyaniline | 4-hydroxyphenyl |
| (g) | 2-hydroxyaniline | 2-hydroxyphenyl |

TABLE I-continued

| | Aniline Replacement (RNH$_2$) | Compound (III) (X = Cl R$_1$ = C$_2$H$_5$) Obtained R |
|---|---|---|
| (h) | 2-hydroxy-4-fluoroaniline | 2-hydroxy-4-fluorophenyl |
| (i) | 2,4-dihydroxyaniline | 2,4-dihydroxyphenyl |
| (j) | p-cyanoaniline | p-cyanophenyl |
| (k) | 2,4-diaminobenzene | p-aminophenyl |
| (l) | p-dimethylaminoaniline | p-dimethylaminophenyl |
| (m) | p-methylmercaptoaniline | p-methylmercaptophenyl |
| (n) | p-aminothiophenol | p-mercaptophenyl |
| (o) | 4-amino-3-methylpyridine | 3-methyl-4-pyridyl |
| (p) | 4-aminopyridine | 4-pyridyl |
| (q) | 3-aminopyrazine | 3-pyrazinyl |
| (r) | 2-aminothiazole | 2-thiazoyl |
| (s) | 3-aminofuran | 3-furyl |
| (t) | 3-aminothiophene | 3-thienyl |
| (u) | 3-chloro-4-hydroxyaniline | 3-chloro-4-hydroxyphenyl |
| (v) | 3,4-methylenedioxyaniline | 3,4-methylenedioxyphenyl |

EXAMPLE 22

In the described fashion of Example 1(f), replacing the acid ester (III) ($R_1$=phenyl, X=Cl, $R_1$=$C_2H_5$) with the acid ester (III) of the compounds listed in Table I of Example 21 and also replacing N-acetylpiperazine with an appropriate amine such as N-methylpiperazine, N-acyl piperazine, pyrrolidine, 3-hydroxypyrrolidine, 3-acetamidopyrrolidine, 3-dimethylaminopyrrolidine, piperidine, morpholine, thiomorpholine, 2,6-dimethylpiperazine, homopiperazine, dimethylamine and 2,2-dimethylhydrazine, one can obtain the following additional compounds as summarized in Table II.

TABLE II

| | acetyl piperazine replacement ZH | Compound III Used X = Cl, R$_1$ = C$_2$H$_5$, R | Compound I Obtained (R$_1$ = H) R | Z |
|---|---|---|---|---|
| 1. | piperazine | 4'-hydroxyphenyl | 4'-hydroxyphenyl | piperazinyl |
| 2. | piperazine | p-methoxyphenyl | p-methoxyphenyl | piperazinyl |
| 3. | piperazine | p-mercaptophenyl | p-mercaptophenyl | piperazinyl |
| 4. | N—methylpiperazine | 4'-hydroxyphenyl | 4'-hydroxyphenyl | N—methylpiperazinyl |
| 5. | M—methylpiperazine | 4'-pyridyl | 4'-pyridyl | N—methylpiperazinyl |
| 6. | N—methylpiperazine | 3'-methyl-4'-pyridyl | 3'-methyl-4'-pyridyl | N—methylpiperazinyl |
| 7. | pyrrolidine | o-fluorophenyl | o-fluorophenyl | pyrrolidinyl |
| 8. | pyrrolidine | p-dimethylaminophenyl | p-dimethylaminophenyl | pyrrolidinyl |
| 9. | 3-hydroxypyrrolidine | o-fluorophenyl | o-fluorophenyl | 3-hydroxypyrrolidinyl |
| 10. | 3-hydroxypyrrolidine | p-chlorophenyl | p-chlorophenyl | 3-hydroxypyrrolidinyl |
| 11. | 3-acetamido-pyrrolidine | o-fluorophenyl | o-fluorophenyl | 3-aminopyrrolidinyl |
| 12. | 3-acetamido-pyrrolidine | p-methylphenyl | p-methylphenyl | 3-aminopyrrolidinyl |
| 13. | 3-dimethylamino-pyrrolidine | p-fluorophenyl | p-fluorophenyl | 3-dimethylaminopyrrolidinyl |
| 14. | piperidine | o-fluorophenyl | o-fluorophenyl | piperadinyl |
| 15. | piperidine | 3-pyrazinyl | 3-pyrazinyl | piperidinyl |
| 16. | piperidine | 3-furyl | 3-furyl | piperidinyl |
| 17. | piperidine | 3-thienyl | 3-thienyl | piperidinyl |
| 18. | morpholine | o-fluorophenyl | o-fluorophenyl | morpholinyl |
| 19. | morpholine | 2,4-dihydroxy-phenyl | 2,4-dihydroxy-phenyl | morpholinyl |
| 20. | morpholine | p-methoxyphenyl | p-methoxyphenyl | morpholinyl |
| 21. | thiomorpholine | o-fluorophenyl | o-fluorophenyl | thiomorpholinyl |
| 22. | thiomorpholine | o-fluorophenyl | o-fluorophenyl | thiomorpholinyl |
| 23. | 2,6-dimethyl-piperazine | o-fluorophenyl | o-fluorophenyl | 3,5-dimethylpiperazinyl |
| 24. | homopiperazine | o-fluorophenyl | o-fluorophenyl | homopiperazinyl |
| 25. | dimethylamine | p-methylphenyl | p-methylphenyl | dimethylamino |
| 26. | 2,2-dimethyl-hydrazine | p-chloroethylphenyl | p-chloroethylphenyl | 2,2-dimethylhydrazyl |
| 27. | thiomorpholine | 2-hydroxy-4-fluorophenyl | 2-hydroxy-4-fluorophenyl | thiomorpholinyl |
| 28. | morpholine | p-cyanophenyl | p-cyanophenyl | morpholinyl |

TABLE II-continued

| acetyl piperazine replacement ZH | Compound III Used X = Cl, R₁ = C₂H₅, R | Compound I Obtained (R₁ = H) R | Z |
|---|---|---|---|
| 29. morpholine | p-aminophenyl | p-aminophenyl | morpholinyl |
| 30. piperidine | p-methylmercapto-phenyl | p-methylmercapto-phenyl | piperidinyl |
| 31. piperazine | 3-chloro-4-hydroxy-phenyl | 3-chloro-4-hydroxy-phenyl | piperazinyl |
| 32. N—methyl-piperazine | 3-chloro-4-hydroxy-phenyl | 3-chloro-4-hydroxy phenyl | 4-methylpiperazinyl |
| 33. 4-acetyl-piperazine | p-fluorophenyl | p-fluorophenyl | 4-acetylpiperazinyl |
| 34. 4-propionyl-piperazine | p-fluorophenyl | p-fluorophenyl | 4-propionyl-piperazinyl |
| 35. piperazine | 3-fluoro-4-hydroxy-phenyl | 3-fluoro-4-hydroxy-phenyl | piperazinyl |
| 36. piperazine | 3,4-methylenedioxy-phenyl | 3,4-methylenedioxy-phenyl | piperazinyl |
| 37. N—methylpiperazine | 3,4-methylenedioxy-phenyl | 3,4-methylenedioxy-phenyl | 4-methyl-piperazinyl |

It will be understood that various changes and modifications can be made in the details of procedure, formulation and use without departing from the spirit of the invention, especially as defined in the following claims.

What is claimed is:

1. A compound having the formula

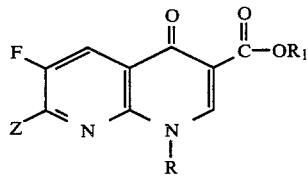

wherein $R_1$ is hydrogen or a carboxy protecting group which with the remainder of the carboxy group completes a carboxylic acid ester group; R is selected from the group consisting of (1) an aromatic heterocyclic ring containing 5 to 6 atoms therein, with 1 to 2 hetero atoms being selected from the group consisting of S, O and N and the remaining atoms in the ring being carbon atoms and substituted derivatives of said aromatic heterocyclic ring wherein the aromatic heterocyclic ring is mono-substituted with $C_1$ to $C_6$ alkyl; and (2) a phenyl group having the formula:

wherein $R_2$ is one, two or three substituents independently selected from the group consisting of hydrogen, halogen, cyano, $C_1$ to $C_6$ alkyl, halo-substituted $C_1$ to $C_6$ alkyl, a group having the formula:

—Y—R₃ wherein —Y— is —O— or —S— and $R_3$ is hydrogen or $C_1$ to $C_6$ alkyl, and $NH_2$; and Z is selected from the group consisting of (1) a heterocyclic ring having the structure:

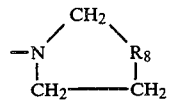

wherein $R_8$ is $CH_2$, $(CH_2)_2$ or a group of the formula —$(CH_2)_n$—$R_9$— wherein $R_9$ is —N—, —O—, or —S— and n is 0, 1 or 2, and substituted derivatives thereof wherein the heterocyclic ring is substituted with one, two or three substituents independently selected from the group consisting of $C_1$ to $C_6$ alkyl, $C_1$ to $C_3$ alkylamino-substituted $C_1$ to $C_6$ alkyl, amino-substituted $C_1$ to $C_6$ alkyl, hydroxy, alkanoyl containing 1 to 6 carbon atoms, alkanoylamido containing 1 to 6 carbon atoms, halogen, an amine of the formula:

wherein $R_{10}$ and $R_{11}$ are each independently selected from the group consisting of hydrogen and $C_1$ to $C_6$ alkyl; and (2) an amino group of the formula:

wherein $R_6$ is hydrogen or $C_1$ to $C_6$ alkyl, and $R_7$ is selected from the group consisting of $C_1$ to $C_6$ alkyl, $NH_2$, a mono-($C_1$ to $C_4$)alkylamino group and a di-($C_1$ to $C_4$)alkylamino group, and pharmaceutically acceptable salts thereof.

2. A compound as defined in claim 1 wherein Z is selected from the group consisting of piperazinyl, piperidinyl, pyrrolidinyl, morpholino, thiomorpholino and homopiperazinyl and substituted derivatives thereof.

3. A compound as defined in claim 1 wherein the aromatic heterocyclic group is selected from the group consisting of pyridyl, pyrazinyl, thiazolyl, furyl, thienyl.

4. A compound as defined in claim 1 wherein $R_1$ is hydrogen.

5. A compound as defined in claim 1 wherein Z is an amino group having the formula:

wherein $R_6$ is hydrogen or $C_1$ to $C_6$ alkyl, and $R_7$ is $C_1$ to $C_6$ alkyl, $NH_2$, a mono-($C_1$ to $C_4$)alkylamino group or a di-($C_1$ to $C_4$)alkylamino group.

6. A compound having the formula:

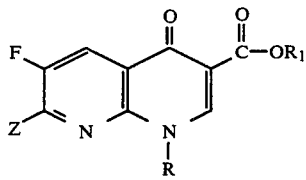

wherein Z is (1) mono- or di-substituted 1-pyrrolidinyl wherein the substituent is independently selected from $NH_2$, $C_1$ to $C_3$ alkyl, halogen, amino-substituted $C_1$ to $C_6$ alkyl and $C_1$ to $C_3$ alkylamino-substituted $C_1$ to $C_6$ alkyl, or (2) 1-piperazinyl or substituted 1-piperazinyl wherein the substituent on the piperazinyl is one, two or three substituents independently selected from $C_1$ to $C_6$ alkyl, or $C_1$ to $C_6$ alkanoyl; $R_1$ is hydrogen or a carboxy protecting group which with the remainder of the carboxy group completes a carboxylic acid ester group; and R is phenyl or substituted phenyl wherein the substituent on the phenyl group is one, two or three substituents independently selected from $C_1$ to $C_6$ alkyl, halogen, methylenedioxy and hydroxy and pharmaceutically acceptable salts thereof.

7. A compound as defined in claim 6 wherein R is p-fluorophenyl, Z is 1-piperazinyl and $R_1$ is hydrogen.

8. A compound as defined in claim 6 wherein R is p-fluorophenyl, Z is 4-methyl-1-piperazinyl and $R_1$ is hydrogen.

9. A compound as defined in claim 6 wherein R is p-fluorophenyl, Z is 3-methyl-1-piperazinyl and $R_1$ is hydrogen.

10. A compound as defined in claim 6 wherein R is p-fluorophenyl, Z is 3-amino-4-methyl-1-pyrrolidinyl and $R_1$ is hydrogen.

11. A compound as defined in claim 6 wherein $R_1$ is hydrogen, R is p-fluorophenyl and Z is 3-amino-1-pyrrolidinyl.

12. A compound as defined in claim 6 wherein R is o,p-difluorophenyl, Z is 3-methyl-1-piperazinyl and $R_1$ is hydrogen.

13. A compound as defined in claim 6 wherein R is o,p-difluorophenyl, Z is 1-piperazinyl and $R_1$ is hydrogen.

14. A compound as defined in claim 6 wherein R is o,p-difluorophenyl, Z is 3-amino-4-methyl-1-pyrrolidinyl and $R_1$ is hydrogen.

15. A compound as defined in claim 6 wherein R is o,p-difluorophenyl, Z is 3-aminomethyl-4-chloro-1-pyrrolidinyl and $R_1$ is hydrogen.

16. A compound as defined in claim 6 wherein R is o,p-difluorophenyl, Z is 3-ethylaminomethyl-1-pyrrolidinyl and $R_1$ is hydrogen.

17. A compound as defined in claim 6 wherein $R_1$ is hydrogen, R is o,p-difluorophenyl and Z is 3-amino-1-pyrrolidinyl.

18. A compound as defined in claim 6 wherein $R_1$ is hydrogen, R is o,p-difluorophenyl and Z is 4-methyl-1-piperazinyl.

19. A composition having antibacterial activity in pharmaceutical dosage form containing a diluent and a compound as defined in claim 1.

20. A composition having antibacterial activity in pharmaceutical dosage form containing a diluent and a compound as defined in claim 6.

21. A method of treating a bacterial infection in a patient comprising administering to a patient in need a therapeutically effective amount of a compound as defined in claim 1.

22. A method of treating a bacterial infection in a patient comprising administering to a patient in need a therapeutically effective amount of a compound as defined in claim 6.

* * * * *

UNITED STATES PATENT AND TRADEMARK OFFICE
CERTIFICATE OF CORRECTION

PATENT NO. : 4,616,019
DATED : October 7, 1986
INVENTOR(S) : DANIEL T. CHU

It is certified that error appears in the above-identified patent and that said Letters Patent is hereby corrected as shown below:

Column 7, line 60, "2.54" should read --0.54--.

Signed and Sealed this

Second Day of June, 1992

*Attest:*

DOUGLAS B. COMER

*Attesting Officer*      *Acting Commissioner of Patents and Trademarks*